United States Patent [19]

Fruhwith et al.

[11] 3,998,706
[45] Dec. 21, 1976

[54] PROCESS FOR THE SEPARATION OF CHLOROHYDROCARBONS FROM LOWER BOILING IMPURITIES

[75] Inventors: Otto Fruhwirt; Hellmuth Frey, both of Burghausen; Ludwig Schmidhammer, Haiming, all of Germany

[73] Assignee: Wacker-Chemie GmbH, Munich, Germany

[22] Filed: Aug. 13, 1975

[21] Appl. No.: 604,395

[30] Foreign Application Priority Data

Sept. 23, 1974 Germany .................. 2445371

[52] U.S. Cl. .................... 203/7; 203/38; 203/53; 203/59; 203/87; 203/93; 203/97; 203/29; 260/652 P
[51] Int. Cl.² .......................... B01D 3/34
[58] Field of Search ............. 203/7, 36–38, 203/40, 87, 94, 98, 29, 39, 53, 59, 93, 96, 97; 260/652 P

[56] References Cited

UNITED STATES PATENTS

| 2,589,212 | 3/1952 | Agapetus | 203/37 |
| 2,908,640 | 10/1959 | Dougherty | 203/7 |
| 3,676,327 | 7/1972 | Foroulis | 203/7 |
| 3,779,905 | 12/1973 | Stedman | 203/7 |
| 3,790,496 | 2/1974 | Hausler | 203/7 |
| 3,846,253 | 11/1974 | Obrecht | 203/7 |

FOREIGN PATENTS OR APPLICATIONS 630,074   7/1963   Belgium .................. 260/652 P Primary Examiner—Hiram H. Bernstein
Attorney, Agent, or Firm—Allison C. Collard

[57] ABSTRACT

A process for separating lower-boiling chlorohydrocarbons and water from neutralized crude chlorohydrocarbons having at least two carbon atoms, which comprises fractionally distilling the crude chlorohydrocarbons in a fractionating column, thereby obtaining a fraction A containing the desired product which is withdrawn at the bottom of the column practically free of impurities, and a fraction B, comprising water, impurities having a lower boiling point, and entrained amounts of the desired chlorohydrocarbon, withdrawing said fraction B from the top of the column and, while still in gaseous state, neutralizing fraction B with an aqueous solution of a mixture of basic compounds, thereby avoiding corrosion of the apparatus, and thereafter subjecting the gaseous fraction to stepwise condensation with recovery of the entrained portions of said chlorohydrocarbon by returning them to the fractionating column, while separately removing water and undesirable impurities.

8 Claims, 1 Drawing Figure

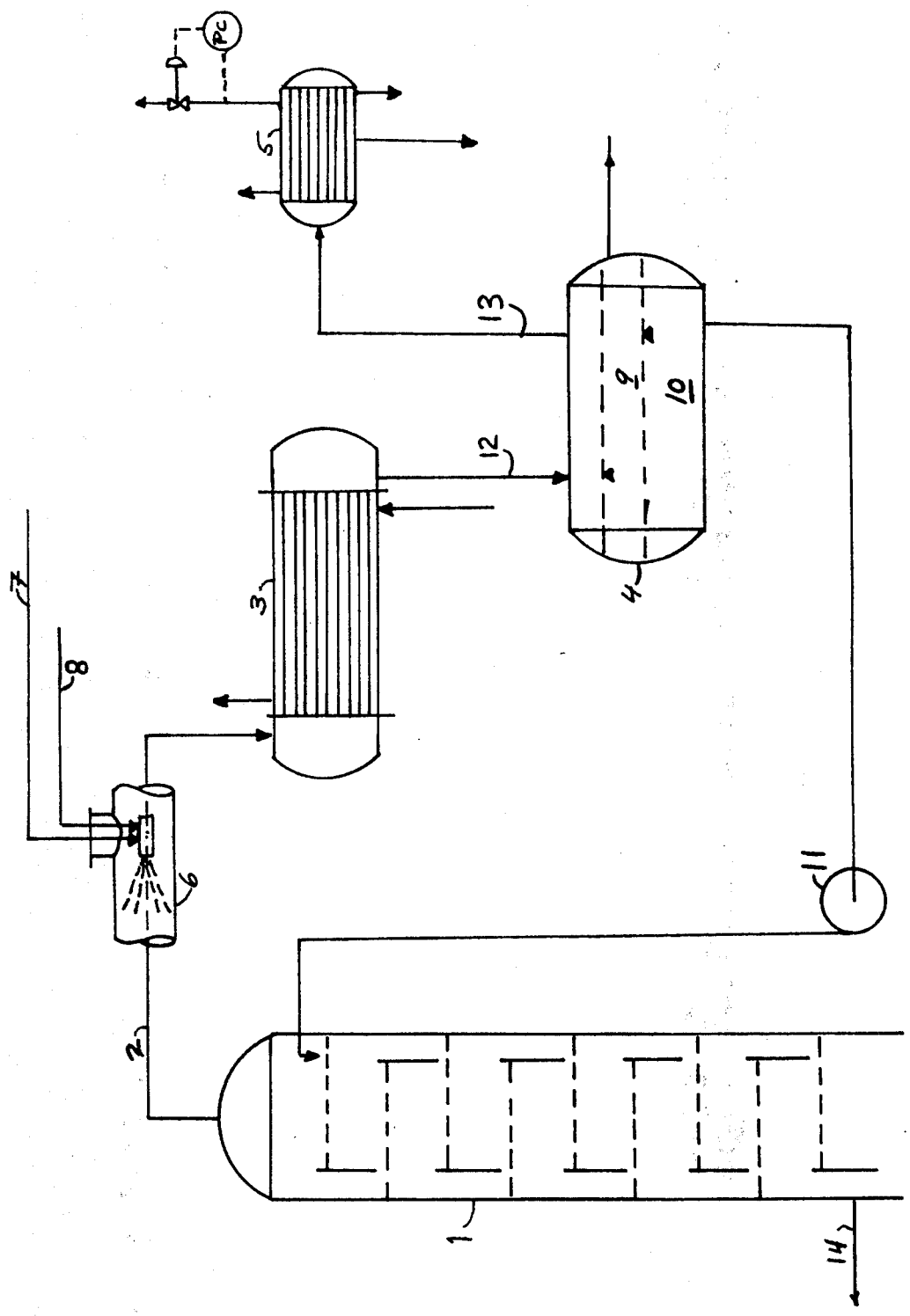

PROCESS FOR THE SEPARATION OF CHLOROHYDROCARBONS FROM LOWER BOILING IMPURITIES

The present invention relates to a process for the separation of lower boiling chlorinated compounds from chlorohydrocarbons having at least two carbon atoms, and especially from 1,2-dichloroethane.

Various industrial processes are used for the large-scale manufacture of chlorohydrocarbons having at least two carbon atoms; most of these processes yield a crude product, which contains various amounts of undesirable chlorinated products having low boiling points as well as hydrogen chloride and dissolved chlorine. The inorganic impurities can be removed by washing and neutralisation with aqueous alkali. The aqueous phase can then be separated off to leave a moist neutralized crude product. This product then has to be purified by distillation to remove the water and those impurities having a boiling point lower than that of the desired chlorohydrocarbon (hereinafter referred to as "lower-boiling impurities"), and it is with such purification that this invention is primarily concerned.

The water and lower-boiling impurities can be removed in a combined process consisting essentially of azeotropic drying by boiling while simultaneously removing the lower-boiling impurities by fractional distillation. A fraction consisting of water, the lower-boiling impurities, and portions of the desired chlorohydrocarbon accumulates at the top of the column, whereas the sump fraction consists mainly of the desired chlorohydrocarbon and small amounts of higher-boiling impurities. A disadvantage of this process is that the desired chlorohydrocarbon is discharged via the top of the column together with the water and the lower-boiling impurities. This results in some loss of the desired product unless the expensive step of a further distillation is carried out.

Another difficulty in this process is the problem of corrosion. Small amounts of hydrogen chloride and chlorine split off from the chlorohydrocarbons in the lower part of the fractionating column, and leave the top of the column together with the water and lower-boiling impurities. Condensation of this mixture results in the formation of aqueous hydrochloric acid and aqueous hypochlorous acid, which can have a severe corrosive effect on the condensation apparatus. Aqueous alkaline solutions have been introduced into the mixture prior to condensation in order to neutralize the gases (German Democratic Republic Patent Specification No. 100,933), but the effect of this is limited, because it is not, in practice, possible to achieve any substantial neutralization of impurities contained in chlorohydrocarbons by means of aqueous alkali alone. An alternative method of neutralization is by blowing in ammonia, but ammonium chloride then precipitates since it is not soluble in chlorohydrocarbons. The precipitated ammonium chloride can cause corrosion and can block parts of the apparatus.

It is an object of the present invention to provide a process for the separation of lower-boiling impurities and water from the desired main product contained in a moist neutralized crude chlorohydrocarbon in such a manner that as little as possible of the main product gets lost.

It is a further object of the present invention to provide a process which prevents corrosion, and secures a long life of the apparatus used in the process.

The invention therefore consists of a process for separating lower-boiling chlorohydrocarbons and water from neutralized crude chlorohydrocarbons having at least two carbon atoms, which comprises the steps of:

a. fractionally distilling the crude chlorohydrocarbon in a fractionating column, thereby obtaining a fraction A containing the desired product and a gaseous fraction B comprising water, impurities having a lower-boiling point than that of the desired chlorohydrocarbon, and entrained amounts of said desired chlorohydrocarbon;

b. removing the gaseous fraction from the top of the column;

c. mixing the fraction while still gaseous with water vapor, an aqueous solution of a basic alkali metal compound, and an aqueous solution of ammonia and/or an amine;

d. cooling the gaseous fraction by condensation to such a temperature that only the water and a major portion of the chlorohydrocarbon condenses into a liquid phase while a major portion of the lower-boiling impurities remains in the gaseous phase;

e. separating the gaseous phase from the liquid phase and condensing it;

f. separating the liquid phase into an aqueous phase and an organic phase;

g. conveying the organic phase back into the fractionating column; and h. removing purified chlorohydrocarbon from the lower part of the column.

This process has considerable advantages due to the described combination of operations. Thus, due to the condensation of the gaseous fraction in two steps instead of one, the loss of desired chlorohydrocarbon entrained in the waste products is reduced. Also, there is both an improvement in the yield of the desired chlorohydrocarbon, and a reduction in the quantity of waste product, with a resultant reduction in pollution of the environment. A further advantage is that the addtion of the water vapor aqueous ammonia and/or amine as the above-specified aqueous alkaline solutions results in relatively little corrosion of the apparatus as compared with the previously mentioned processes. Consequently, the apparatus has a longer life.

The chlorohydrocarbons to be purified according to present invention are those having from 2 to 4 carbon atoms; they may be either saturated or unsaturated. Advantageously, they also have 2, 3, or 4 chlorine atoms. Examples of such compounds are 1,1-dichloroethane, 1,2-dichloroethane, 1,1,1-trichloroethane, trichloroethylene, perchloroethylene, 1,2-dichloropropane, and chlorobutane. The process is of particular importance for obtaining pure 1,2-dichloroethane.

The above compounds are generally obtained by oxychlorination, chlorine addition, HCl splitting and similar known methods. In the process, acidic compounds are always formed, which are washed with aqueous alkali metal solutions and neutralized. After separating the aqueous phase, the moist neutral chlorohydrocarbon is obtained which is the crude product of this invention still containing lower boiling and higher boiling undesirable chlorohydrocarbons as impurities.

As mentioned above, lower boiling hydrocarbons are the ones having a lower boiling point than the one of the desired product of the invention. For instance, in 1,2-dichloroethane, there are chloroethane, chloroform and carbon tetrachloride present as impurities. As to the higher-boiling compounds, they do not play any significant role in the present process, because they remain in the main product and a special operation is necessary for their removal.

The present process can be carried out either continuously or discontinuously, but it is of particular importance for a continuous method of operation.

The first step of the process is the fractional distillation of the crude chlorohydrocarbon. This may be carried out using a conventional fractionating column having several plates. The temperature within the fractionating column will depend on the particular chlorohydrocarbon to be purified. In the case of 1,2-dichloroethane, the temperature in the sump is advantageously from 120° to 130° C, and the temperature at the top of the column is advantageously from 90° to 100° C. at a pressure of about 2 atmospheres gauge.

The distillation may be carried out under atmospheric pressure or under superatmospheric pressure. The latter is often advantageous as it may enable the lower boiling impurities to be condensed, in the second condensation step, step (e), by normal cooling water. The actual pressure chosen will depend on the boiling points of the lower boiling impurities to be removed, but in most cases, a pressure of from 1 to 5 atmospheres gauge, preferably from 1.5 to 3 atmospheres gauge, throughout the entire purification system is suitable.

The main product, fraction A, is withdrawn from the bottom of the column.

A gaseous fraction B comprising water vapor, lower boiling impurities, and entrained portions of the desired chlorohydrocarbon is removed from the top of the fractionating column by a vapor conduit into a condenser.

While fraction B is still gaseous, it is mixed with water vapor, an aqueous solution of a basic alkali metal compound, and an aqueous solution of ammonia and/or of an amine. This can conveniently be achieved by metering these solutions and the water vapor into the vapor conduit. The point at which these components are metered in is not generally critical, except that, of course, it should be at a point where the fraction is still gaseous and should not be so near the top of the column as substantially to disturb the distillation balance in the column.

The two aqueous solutions may be introduced in the form of a mixed aqueous solution, but they may, alternatively be introduced separately. In the latter case, however, it is advantageous for the ammonia/amine solution to be introduced together with the water vapor. It is, in most cases, expedient to use a single mixed aqueous solution, and this may be sprayed into the vapor conduit together with the water vapor by means of a two-way nozzle. It is advantageous to introduce these components in counter-current to the gaseous fraction B.

When using a mixed aqueous solution of the alkali metal compound and the ammonia/amine, it is desirable for the solution to contain from 0.05 to 25%, preferably from 0.5 to 1%, by weight of the alkali metal compound, and a total of from 0.05 to 5%, preferably from 0.1 to 0.5%, by weight of ammonia and/or of the amine.

The production of a mixed aqueous solution of a basic alkali metal compound and ammonia and/or an amine can conveniently be effected in a vessel provided with a stirrer, by introducing, via a suitable measuring device, gaseous ammonia from a cylinder and/or gaseous amine into an aqueous solution of the alkali metal compound. In the case of liquid amines, these can conveniently be added in premeasured amounts.

Suitable basic alkali metal compounds are, for example, alkali metal hydroxides, such as lithium-sodium-, and potassium hydroxides, alkali metal carbonates, and bicarbonates, e.g., lithium carbonate, soda, potassium carbonate and potash; sodium and potassium bicarbonates; and mixtures of two or more thereof. Suitable amines are, advantageously, aliphatic amines, preferably having up to four carbon atoms, for example, methylamine, dimethylamine, trimethylamine, ethylamine, diethylamine, propylamine, isobutylamine, t-butylamine, and 1-sec-butylamine; also diamines, for example, ethylenediamine, may be used. Mixtures of two or more amines or of one or more amines with ammonia may also be used. The boiling point of the amine used should not be greater than that of the chlorohydrocarbon to be purified, otherwise it will not be separated from the chlorohydrocarbon in the subsequent process steps.

The amount of alkali metal compound and ammonia/amine mixed with the gaseous fraction depends on the amount of acidic components (e.g., decomposed chlorohydrocarbon or hypochlorous acid) in the gaseous fraction. In general, from 0.4 to 0.8 mole of ammonia/amine and from 0.8 to 2 moles, preferably 1 to 1.5 moles, of the alkali metal compound are used per mole of acidic components. It is, however, not generally possible theoretically to predict the degree of decomposition of the chlorohydrocarbon and impurities and thus it is not possible theoretically to calculate the amount of acidic compounds. This has, therefore, to be determined empirically. In the continuous operation of an industrial plant, a convenient way of ascertaining the amount of alkali metal compound and ammonia/amine to be introduced is by measuring the pH-value of aqueous phase obtained from the liquid phase issuing from the first condensation step and adjusting the pH value from 9 to 10 by appropriate addition of the amount of basic components.

The amount of water vapor introduced into the gaseous fraction depends primarily on the amount of aqueous solution(s) introduced, and it is advantageous for the ratio of water vapor to aqueous solution(s) to be from 1 : 1 to 2 : 1. (Excess of vapor.)

By way of example, the continuous purification of 10 t/h of crude 1,2-dichloroethane consisting of about 96 mole % of 1,2-dichloroethane, 0.8 mole % of water, 3 mole % of lower-boiling impurities (e.g., ethyl chloride, chloroform, and 1,1-dichloroethane), and 0.2 mole % of higher-boiling impurities (e.g., 1,1,2-trichloroethylene and higher molecular weight chlorohydrocarbons), generally requires from 100 to 150 kg/h of an aqueous solution containing 0.5 to 0.8% by weight of a basic alkali metal compound and 0.1 to 0.2% by weight of ammonia and/or an amine, and from 150 to 200 kg/h of water vapor.

When the water vapor and the aqueous solutions have been injected into the gaseous fraction B, this fraction is cooled, suitably by passing it into a condenser such that the water and desired chlorohydrocarbon substantially condense into a liquid phase. The temperature to which the gaseous fraction is cooled to achieve the desired condensation depends, of course, on the boiling points of the chlorohydrocarbon and the lower boiling impurities. When the chlorohydrocarbon is 1,2-dichloroethane, it is advantageous to cool the gaseous fraction to a temperature within the range of from 60° to 80° C, preferably from 65° to 75° C.

It was found that, in contrast to previous processes, there is comparatively little, if any, corrosion of the condenser — at conduits or welding seams — used for this cooling step, or in the collector used in the subsequent process step, especially when using apparatus of stainless steel. This is all the more surprising, because the condenser is operated at a higher temperature than in previous processes in which the entire gaseous fraction was condensed.

The gas-liquid mixture resulting from this condensation step is then conveyed into a collecting vessel where it is separated into a gaseous phase and a liquid phase. The liquid phase will drop to the lower region of the vessel and the gaseous phase can leave through an outlet in the upper region of the vessel. The gaseous phase, which now consists substantially of lower-boiling impurities, can then be passed to a second condenser, where the final condensation step can take place. The liquified lower-boiling impurities can then be discharged from this second condensation step.

The liquid phase in the collecting vessel is separated into an aqueous phase and an organic phase. This can conveniently be achieved simply by allowing the liquid to stand and to separate into two phases in the collecting vessel, and drawing off the respective phases through outlets situated at suitable levels in the vessel wall. The aqueous phase may be drawn off and passed, for example, to a waste water treatment plant. The organic phase is returned, with the aid of a pump if necessary, to the fractionating column. This organic phase generally still contains small quantities, for example, 0.01 to 0.1% by weight, of ammonia and/or amine, and this has a stabilizing effect on the chlorohydrocarbon in the fractionating column.

The purified chlorohydrocarbon (but still containing higher-boiling impurities) is drawn off from the lower region of the fractionating column.

The accompanying drawing illustrates schematically a device for carying out the process of the invention.

In the drawing, a fractionating column 1 is shown in direct connection with a vapor conduit 2, arranged in series with a condenser 3. Between conduit 2 and condenser 3, a two-way nozzle 6 is interposed serving for admission lines 7 and 8 for vapor supply and aqueous solution, respectively. From condenser 3, a line 12 leads to a collecting vessel 4 which receives the aqueous phase 9, and the organic phase 10. A pump 11 serves to return the organic phase to fractionating column 1.

A line 13 connects the upper part of the collecting vessel to a second condenser 5, serving for condensation of the gaseous fraction B. Connected to condenser 5 is a pressure control device PC. The main product, fraction A, is withdrawn through a line 14.

The process according to the invention will now be described in general terms with reference to the above-described drawing.

Crude chlorohydrocarbon is introduced into the fractional distillation column 1 through an inlet (not shown), where it is heated to such a temperature that a gaseous fraction comprising primarily water, lower boiling impurities, and entrained chlorohydrocarbon leaves the top of column 1 through vapor conduit 2. Supply pipes 7 and 8 respectively carry water vapor and a mixed aqueous solution of a basic alkali metal compound and of ammonia and/or an amine to the two-way nozzle 6, from which the water vapor and aqueous solution are injected into vapor conduit 2 in counter-current to the still gaseous fraction. The gaseous fraction, water vapor, and aqueous solution are conveyed to condenser 3. This is maintained at such a temperature that a major portion of the water and the chlorohydrocarbon condenses into a liquid phase, while the lower-boiling impurities remain in a gaseous phase. The resulting gas-liquid mixture is passed from condenser 3 to collector 4. The gaseous phase leaves collector 4 through an outlet in its upper region and is passed to second condenser 5, where it is condensed, and the resulting liquified lower boiling impurities are drawn off. The liquid phase drops to the lower region of collector 4, where it separates into an upper aqueous phase 9, which is drawn off, and a lower organic phase 10, which is returned via pump 11 to column 1. The purified chlorohydrocarbon is drawn off from column 1 through a discharge line 14.

The invention will now be further illustrated by means of the following specific example, which was carried out in a plant similar to that schematically shown in the accompanying drawing.

EXAMPLE 10 t/h of crude moist neutralized 1,2-dichloroethane, consisting of about 96 mole % of 1,2-dichloroethane, 0.8 mole % of water, 3 mole % of lower-boiling impurities (e.g., $C_2H_5Cl$, $CHCl_3$, and $CCl_4$), and 0.2 mole % of higher-boiling impurities (e.g., $1,1,2$-$C_2H_3Cl_3$), were introduced into the fractionating column 1. The sump temperature was maintained at 125°–126° C and the temperature at the top of the column at 96°–98° C. The pressure throughout the entire system was maintained at 2 atmospheres gauge, by means of the pressure control device PC. In column 1, the crude 1,2-dichloroethane was subjected to fractional distillation. The gaseous fraction issuing from the top of column 1 was carried off from the column by conduit 2. An aqueous solution containing 0.6 % by weight of NaOH and 0.15% by weight of ammonia was prepared in a stirred vessel and metered, by means of a variable-stroke piston metering pump, at the rate of 120 kg/h into supply pipeline 8. 200 kg/h of water vapor was metered into conduit 7. The water vapor and aqueous solution were injected as a fine spray into the vapor conduit 2 via the two-way nozzle 6, in counter-current to the gaseous fraction. The gaseous fraction, water vapor, and aqueous solution were conveyed into condenser 3. The gas-liquid mixture issuing from this condenser 3 was passed to collector 4. From here, the still gaseous phase was passed to condenser 5 and condensed therein. In collector 4, the liquid phase separated into an aqueous phase 9 and an organic phase 10. The aqueous phase 9 was drawn off. This contained about 0.015% by weight of ammonia and about 0.03% by weight of NaOH. Its pH-value was regularly checked to ensure that it remained between 9 and 10 (had it varied outside this range the amount of aqueous solution introduced via the supply pipe 8 would have been adjusted as necessary). The organic phase 10, which contained about 0.05% by weight of ammonia, was returned via the pump 11 into the column 1. Purified, 1,2-dichloroethane, still containing a small amount of higher boiling impurities, was drawn off from the bottom of column 1.

Organic compounds not condensed at the temperature obtained in condenser 3 were conveyed to condenser 5 and there condensed at lower temperature.

The liquid product obtained from condenser 5 contained only small amounts of 1,2-dichloroethane. The apparatus suffered no appreciable corrosion after 2 years' operation.

Very similar results were obtained when using $Na_2CO_3$ or $NaHCO_3$ or instead of the NaOH, and when using $CH_3NH_2$ instead of the ammonia, combined with water vapor in aqueous solution.

COMPARISON EXAMPLE 1

A similar process was carried out, by way of comparison, but omitting the ammonia, and water vapor. Thus, only NaOH solution was introduced through nozzle 6. It was found that the apparatus suffered severe corrosion with recurring leaks appearing in condenser 3. Condenser 3 had to be replaced after a half-year's operation. Moreover, products from the corrosion accumulated in collector 4.

COMPARISON EXAMPLE 2

By way of further comparison, a similar process was carried out, with condenser 5 being omitted, and with condenser 3 being operated at such temperature that substantially all of the gaseous fraction condensed therein. It was necessary to draw off liquid from organic phase 10 so as to remove the lower boiling impurities from the system and to prevent them accumulating to such a degree that they were drawn off from column 1 with the 1,2-dichloroethane. This liquid withdrawn from the organic phase 10 contained about 30% by weight of 1,2-dichloroethane.

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and intended to be, within the full range of equivalence of the following claims.

What is claimed is:

1. A process for separating lower-boiling chlorohydrocarbons and water from neutralized crude chlorohydrocarbons having from 2 to 4 carbon atoms and from 2 to 4 chlorine atoms, which comprises the steps of
   a. fractionally distilling the crude hydrocarbon in a fractionating column thereby obtaining a fraction A containing the desired product and gaseous fraction B comprising water, impurities having a lower boiling point than that of the desired chlorohydrocarbon, and entrained amounts of said desired chlorohydrocarbon;
   b. removing the gaseous fraction from the top of the column;
   c. mixing the fraction while still in gaseous form with water vapor, an aqueous solution of a basic alkali metal compound containing from 0.05 to 25% by weight of the alkali metal compound and an aqueous solution of ammonia and an aliphatic amine up to 4 C atoms, containing a total of from 0.05 to 5% by weight of ammonia and amine;
   d. cooling said gaseous fraction by condensation to such a temperature that only water and a major portion of the chlorohydrocarbon from fraction B condenses into a liquid phase, while a major portion of the lower-boiling impurities remains in the gaseous phase;
   e. separating the said gaseous phase from said liquid phase and condensing it;
   f. separating said liquid phase into an aqueous phase and an organic phase;
   g. conveying the organic phase back into the fractionating column; and
   h. removing purified chlorohydrocarbon from the lower part of the column.

2. The process as recited in claim 1 wherein the operations are under a pressure of from 1 to 5 atmospheres guage.

3. The process as recited in claim 1 wherein the water vapor and aqueous solutions are introduced into the gaseous fraction in counter-current to the gaseous fraction.

4. The process as recited in claim 1 wherein the ratio of water vapor to aqueous solution is from 1 : 1 to 2 : 1.

5. The process as recited in claim 1 wherein the aqueous phase of step (f) has a pH-value of from 9 to 10.

6. The process as recited in claim 1 wherein the chlorohydrocarbon is 1,2-dichloroethane.

7. The process as recited in claim 6 wherein the temperature of the sump of the fractionating column is from 120° to 130° C, and the temperature at the top of the fractionating column is from 90° to 100° C.

8. The process as recited in claim 6 wherein the temperature to which the gaseous fraction B is cooled is within the range of from 60° to 80° C.

* * * * *